US005799656A

United States Patent [19]
Alfano et al.

[11] Patent Number: 5,799,656
[45] Date of Patent: Sep. 1, 1998

[54] OPTICAL IMAGING OF BREAST TISSUES TO ENABLE THE DETECTION THEREIN OF CALCIFICATION REGIONS SUGGESTIVE OF CANCER

[75] Inventors: Robert R. Alfano, Bronx; Ping-Pei Ho, Great Neck; Leming Wang, Flushing; Xiangchun Liang, Bronx; Pierre A. Galland, Queensvillage, all of N.Y.

[73] Assignee: The Research Foundation of City College of New York, New York, N.Y.

[21] Appl. No.: 733,558

[22] Filed: Oct. 21, 1996

[51] Int. Cl.$^6$ .................................................. A61B 6/00
[52] U.S. Cl. .................. 128/664; 128/665; 250/341.1; 250/358.1
[58] Field of Search .................. 128/664, 665, 128/898; 250/341.1, 358.1

[56] References Cited

U.S. PATENT DOCUMENTS

| | | | |
|---|---|---|---|
| 4,768,516 | 9/1988 | Stoddart et al. | 128/665 |
| 5,227,912 | 7/1993 | Ho et al. | 359/258 |
| 5,371,368 | 12/1994 | Alfano et al. | 250/341.1 |

OTHER PUBLICATIONS

Sickles, "Breast Calcifications: Mammographic Evaluation," Radiology, 160:289–93 (1986).
Wang et al., "Ballistic 2–D Imaging Through Scattering Walls Using an Ultrafast Optical Kerr Gate," Science, 253:769–71 (1991).
Yoo et al., "Imaging through a scattering wall using absorption," Opt. Lett., 16:1068–70 (1991).
Egan et al, "Intramammary Calcifications without an Associated Mass in Benign and Malignant Diseases," Radiology, 137:1–7 (1980).

*Primary Examiner*—George Manuel
*Assistant Examiner*—Eleni Mantis Mercader
*Attorney, Agent, or Firm*—Kriegsman & Kriegsman

[57] ABSTRACT

A method for detecting the presence of one or more calcifications within a portion of a turbid medium, such as a breast tissue. According to one aspect, the method involves illuminating at least a portion of the turbid medium with light, whereby light emerges from the turbid medium consisting of a ballistic component, a snake-like component and a diffuse component, temporally and/or spatially gating the emergent light to preferentially pass the ballistic and/or snake-like components, using the temporally and/or spatially gated light to form an image of the illuminated portion of the turbid medium, and examining the image for the presence of one or more calcifications. Wavelength difference images may also be used to highlight tumors and calcification regions. The foregoing method may be used to form optical images of breast tissues, with the presence in such images of calcifications suggestive of cancer being used to identify the corresponding breast tissues as good candidates for biopsy and screening for tumors.

74 Claims, 2 Drawing Sheets

~150μm

~300μm

OPTICAL IMAGING OF BREAST TISSUES TO ENABLE THE DETECTION THEREIN OF CALCIFICATION REGIONS SUGGESTIVE OF CANCER

BACKGROUND OF THE INVENTION

The present invention relates generally to techniques for imaging objects located in or behind turbid media and more particularly to an optical imaging technique for detecting cancer-suggestive calcification regions in breast tissues and other turbid media.

As can readily be appreciated, there are many situations in which the detection of an object present in a turbid, i.e., highly scattering, medium is highly desirable. For instance, the detection of a tumor embedded within a tissue is one such example. One common technique for detecting tumors in tissues uses X-ray radiation (often referred to as "mammography"). Although X-ray techniques do provide some measure of success in detecting objects located in turbid media, they are not typically well-suited for detecting very small objects, e.g., tumors less than 1 mm in size embedded in tissues, or for detecting objects in thick media. In addition, X-ray radiation can present safety hazards to a person exposed thereto. Ultrasound and magnetic resonance imaging (MRI) offer alternatives to the use of X-rays but have their own drawbacks.

Another technique commonly used to detect objects in turbid media, such as tumors in tissues, is transillumination. Typically in transillumination, visible light is incident on one side of a medium and the light emergent from the opposite side of the medium is used to form an image. Objects embedded in the medium typically absorb the incident light and appear in the image as shadows. Transillumination as a detection technique has been severely limited in those instances in which the medium is thick or the object is small to acquire 1 cm resolution. This is because light scattering within the medium contributes to noise and reduces the intensity of the unscattered light used to form the image shadow. Transillumination has had limited utility in detecting tumors less than about 1 cm because contrast of tumors and tissue is similar.

To improve the detectability of small objects located in a turbid medium using transillumination, many investigators have attempted to selectively use only certain components of the transilluminating light signal. This may be done by exploiting the properties of photon migration through a scattering medium. Photons migrating through a turbid medium have traditionally been categorized into the early portion consisting of (i) the ballistic (coherent) photons which arrive first by traveling over the shortest, most direct path and (ii) the snake (quasi-coherent) photons which arrive within the first δt after the ballistic photons and which deviate, only to a very slight extent, off a straight-line propagation path and the late portion consisting of the diffusive (incoherent) photons which experience comparatively more scattering than do ballistic and snake photons and, therefore, deviate more considerably from the straight-line propagation path followed by ballistic and snake photons.

Because it has been believed that ballistic and snake photons contain the least distorted image information and that diffusive photons lose most of the image information, efforts to make transillumination work most effectively with turbid media have focused on techniques which permit the selective detection of ballistic and snake photons while rejecting diffusive photons. This process of selection and rejection has been implemented in various time-gating, space-gating and time/space-gating techniques. Patents, patent applications and publications which disclose certain of these techniques include U.S. Pat. No. 5,140,463, inventors Yoo et al., which issued Aug. 18, 1992; U.S. Pat. No. 5,143,372, inventors Alfano et al., which issued Aug. 25, 1992; U.S. Pat. No. 5,227,912, inventors Ho et al., which issued Jul. 13, 1993; U.S. Pat. No. 5,371,368, inventors Alfano et al., which issued Dec. 6, 1994; Alfano et al., "Photons for prompt tumor detection," *Physics World*, pp. 37–40 (January 1992); Wang et al., "Ballistic 2-D Imaging Through Scattering Walls Using an Ultrafast Optical Kerr Gate," *Science*, Vol. 253, pp. 769–771 (Aug. 16, 1991); Wang et al., "Kerr-Fourier imaging of hidden objects in thick turbid media," *Optics Letters*, Vol. 18, No. 3, pp. 241–243 (Feb. 1, 1993); Yoo et al., "Time-resolved coherent and incoherent components of forward light scattering in random media," *Optics Letters*, Vol. 15, No. 6, pp. 320–322 (Mar. 15, 1990); Chen et al., "Two-dimensional imaging through diffusing media using 150-fs gated electronic holography techniques," *Optics Letters*, Vol. 16, No. 7, pp. 487–489 (Apr. 1, 1991); Duncan et al., "Time-gated imaging through scattering media using stimulated Raman amplification," *Optics Letters*, Vol. 16, No. 23, pp. 1868–1870 (Dec. 1, 1991), all of which are incorporated herein by reference.

Of the above-referenced documents, U.S. Pat. No. 5,371,368 is illustrative. In this patent, there is disclosed a system for imaging an object in or behind a highly scattering medium, the system including a laser for illuminating the highly scattering medium with a beam of light. The light emerging from the highly scattering medium consists of a ballistic component, a snake-like component and a diffuse component. A 4F Fourier imaging system with a Kerr gate located at 2F is used to form a time-space gated image of the emerging light, the time-space gated image consisting primarily of the ballistic component and the snake-like component. One potential application for the aforementioned system disclosed in the patent is in the detection of breast tumors.

Still other imaging techniques have been devised that make use of diffusive photons. Examples of these techniques include U.S. patent application Ser. No. 08/618,471, inventors Alfano et al., filed Mar. 18, 1996; U.S. patent application Ser. No. 08/384,112, inventors Alfano et al., filed Feb. 3, 1995; and U.S. patent application Ser. No. 08/419,623, inventors Alfano et al., filed Apr. 6, 1995, all of which are incorporated herein by reference.

As can readily be appreciated, not all tumors that may be imaged by the various techniques described above are cancerous tumors, many such tumors being benign tumors. As can also readily be appreciated, it would be unduly burdensome, time-consuming and expensive if every tumor detected by the various imaging techniques identified above were subsequently biopsied to determine whether the detected tumor is malignant or benign. Moreover, it can readily be appreciated that it would be highly desirable to detect signs of cancer in a tissue as soon as possible, even before a detectable tumor mass has developed, so that a biopsy can be performed at the earliest possible time.

To meet the foregoing objectives, certain cancer-suggestive screening techniques have been developed. One such cancer-suggestive screen, which has been used in examining X-ray images of breast tissues, involves looking for the presence of calcification regions that are suggestive of cancer in the X-ray image of the tissue. Calcifications, which are the smallest structures identified in X-ray mammograms, may be either malignant or benign and frequently range in size from about 0.03 mm to 5 mm, with malignant calcifications typically having a size of less than 0.5 mm. Calcification regions are highly scattering in comparison to tumors or normal tissue. The number, size, shape, appearance and arrangement of calcifications in X-rays are all parameters that have been used to characterize tissue samples as being suggestive of either a malignant or benign condition. See e.g., Sickles, "Breast Calcifications: Mammographic Evaluation," *Radiology*, 160:289–93 (1986); and Egan et al., "Intramammary Calcifications without an Associated Mass in Benign and Malignant Diseases," *Radiology*, 137:1–7 (1980), both of which are incorporated herein by reference.

It should be appreciated, however, that because of the relatively small size of most calcifications, the above-described technique of using calcifications to characterize tissue samples has heretofore been confined to the examination of X-ray images and has not been applied to transillumination techniques.

SUMMARY OF THE INVENTION

It is an object of the present invention to provide a new technique for cancer-screening breast tissues and the like.

It is another object of the present invention to provide a technique as described above that does not involve the use of X-rays or other forms of unsafe ionizing radiation.

Additional objects, features, aspects and advantages of the present invention will be set forth in part in the description which follows, and in part will be obvious from the description or may be learned by practice of the invention. Various embodiments of the invention will be described in sufficient detail to enable those skilled in the art to practice the invention, and it is to be understood that other embodiments may be utilized and that changes may be made without departing from the scope of the invention. The following detailed description is, therefore, not to be taken in a limiting sense, and the scope of the present invention is best defined by the appended claims.

The present invention is based, in part, on the surprising discovery that calcifications of the type that are suggestive of cancer and that are present in breast tissues or similarly turbid media can be detected using optical imaging (e.g., transillumination) wherein time and/or space gating is used to preferentially select the ballistic and/or snake components of the light emergent from the illuminated medium. The diffusive component of the light emergent from the illuminated medium, either by itself or in addition to the ballistic and snake components of the light emergent from the illuminated medium, can also be used to detect calcifications in breast tissues or similarly turbid media; however, the resolution of such images will often be more limited.

Therefore, according to one aspect, the present invention relates to a method for imaging a turbid medium containing one or more calcifications, said method comprising the steps of: (a) illuminating at least a portion of the turbid medium containing at least one calcification with light, whereby light emerges from the turbid medium consisting of a ballistic component, a snake-like component and a diffuse component; (b) gating the emergent light to preferentially pass the ballistic and/or snake-like components; and (c) using the gated light to form an image of the at least one calcification within the illuminated portion of the turbid medium.

According to another aspect, the present invention relates to a method for detecting the presence of one or more calcifications within a portion of a turbid medium, said method comprising the steps of: (a) illuminating at least said portion of the turbid medium with light, whereby light emerges from the turbid medium consisting of a ballistic component, a snake-like component and a diffuse component; (b) gating the emergent light to preferentially pass the ballistic and/or snake-like components; (c) using the gated light to form an image of the illuminated portion of the turbid medium; and (d) examining the image for the presence of one or more calcifications.

According to still another aspect, the present invention relates to a method for cancer-screening a breast tissue, said method comprising the steps of: (a) illuminating at least a portion of a breast tissue with light, whereby light emerges therefrom consisting of a ballistic component, a snake-like component and a diffuse component; (b) gating the emergent light to preferentially pass the ballistic and/or snake-like components; (c) using the gated light to form an image of the illuminated portion of the breast tissue; and (d) examining the image for the presence of calcifications suggestive of cancer.

Preferably, the light used to illuminate the breast tissue under evaluation has a wavelength in the spectral range of about 700 nm to 1350 nm and may be derived from either a pulsed or continuous-wave light source (lamp or laser), with laser light being particularly preferred. The gating step preferably comprises temporally and/or spatially gating the emergent light to selectively pass the ballistic and snake-like components.

Temporal gating of the light emergent from the breast tissue may be achieved, for example, by passing the emergent light through a Kerr gate which is opened for an appropriately short period of time to selectively pass the ballistic and snake components, but not the diffuse components, of the emergent light. Alternatively, two or more synchronized or nonsynchronized Kerr gates may be used to temporally gate the emergent light. Other time-gating devices, such as streak cameras, time-gate image intensifier-CCD cameras, upper-conversion gates, phase-conjugation gates, and the like, may be used instead of or in addition to the aforementioned Kerr gate(s).

Spatial gating of the light emergent from the breast tissue may be achieved, for example, by passing the emergent light through a mechanical aperture placed at the 2F spectral plane of a 4F imaging system, the aperture being appropriate sized to selectively filter out the component of the light exiting the illuminated breast tissue at large angles, i.e., primarily the diffuse component. Other similar space-gating devices may be used instead of or in addition to the aforementioned space-gate.

In a preferred embodiment, time-gating and space-gating of the emergent light are both achieved by positioning the Kerr cell of a Kerr gate at the 2F spectral plane of a 4F Fourier imaging system and by pumping, at the appropriate time synchronized with the arrival of the ballistic and snake-like components thereat, only that portion of the Kerr cell situated at the focal point of the 4F Fourier imaging system.

According to a further aspect, the present invention relates to a method for imaging a turbid medium containing one or more calcifications, said method comprising the steps of: (a) illuminating at least a portion of the turbid medium containing at least one calcification with light, whereby light consisting of a ballistic component, a snake component and a diffuse component emerges from the turbid medium; and (b) forming an image of the at least one calcification within the illuminated portion of the turbid medium with the emergent light.

Instead of using all three components of the emergent light to form the image of the at least one calcification within the illuminated portion of the turbid medium, one could form the image using only the diffusive component of the emergent light or a portion of the diffusive component, as in the above-mentioned U.S. patent application Ser. Nos. 08/618,471, 08/384,112, and 08/419,623.

According to yet a further aspect, the present invention relates to a method for detecting the presence of one or more calcifications within a portion of a turbid medium, said method comprising the steps of: (a) illuminating at least said portion of the turbid medium with light, whereby light emerges from the turbid medium consisting of a ballistic component, a snake-like component and a diffuse component; (b) forming an image of the illuminated portion of the turbid medium with the emergent light; and (c) examining the image for the presence of one or more calcifications.

Instead of using all three components of the emergent light to form the image of the illuminated portion of the turbid medium, one could use only the diffusive component or a portion thereof, as in the above-mentioned U.S. patent application Ser. Nos. 08/618,471, 08/384,112, and 08/419,623.

According to still yet a further aspect, the present invention relates to a method for cancer-screening a breast tissue, said method comprising the steps of: (a) illuminating at least a portion of a breast tissue with light, whereby light emerges therefrom consisting of a ballistic component, a snake-like component and a diffuse component; (b) forming an image of the illuminated portion of the breast tissue with the emergent light; and (c) examining the image for the presence of calcifications suggestive of cancer.

Instead of using all three components of the emergent light to form the image of the illuminated portion of the breast tissue, one could use only the diffusive component or a portion thereof, as in the above-mentioned U.S. patent application Ser. Nos. 08/618,471, 08/384,112, and 08/419,623.

For purposes of the present specification and claims, the term "transillumination," when used in reference to the present invention, is not intended to be limited solely to techniques comprising the illumination of one side of an object and the formation of an image of the object using the light emergent from the opposite side of the object (such as frequency modulation method), but rather, is intended to encompass broadly any technique comprising the illumination of one side of an object and the formation of an image of the object using the light emergent from either the illuminated or any other side of the object.

BRIEF DESCRIPTION OF THE DRAWINGS

The accompanying drawings, which are hereby incorporated into and constitute a part of this specification, illustrate various embodiments of the invention and, together with the description, serve to explain the principles of the invention. In the drawings wherein like reference numerals represent like parts.

DETAILED DESCRIPTION OF PREFERRED EMBODIMENTS

The present invention is based, at least in part, on the unexpected discovery that calcifications of the type that are present in breast tissues and that can be used to screen for cancer can be detected using optical imaging (e.g., transillumination) wherein time and/or space gating is used to preferentially select the ballistic and/or snake components, as opposed to the diffuse components, of the light emergent from the illuminated tissue. Diffuse light can also be used in a limited way to see calcifications with some resolution. As noted above, calcifications have previously been detected using X-ray techniques; however, prior to the present invention, optical imaging techniques, such as transillumination (with or without gating), had not been investigated to detect calcifications. We teach that calcification regions are highly scattering and even these small regions will be apparent on a transillumination shadowgram. These images can be found by time-resolved or frequency modulation methods since the two methods are connected by a Fourier transform (time $\leftrightarrow$ frequency). Time domain profiles give all frequencies necessary to form a range.

Figure 1:
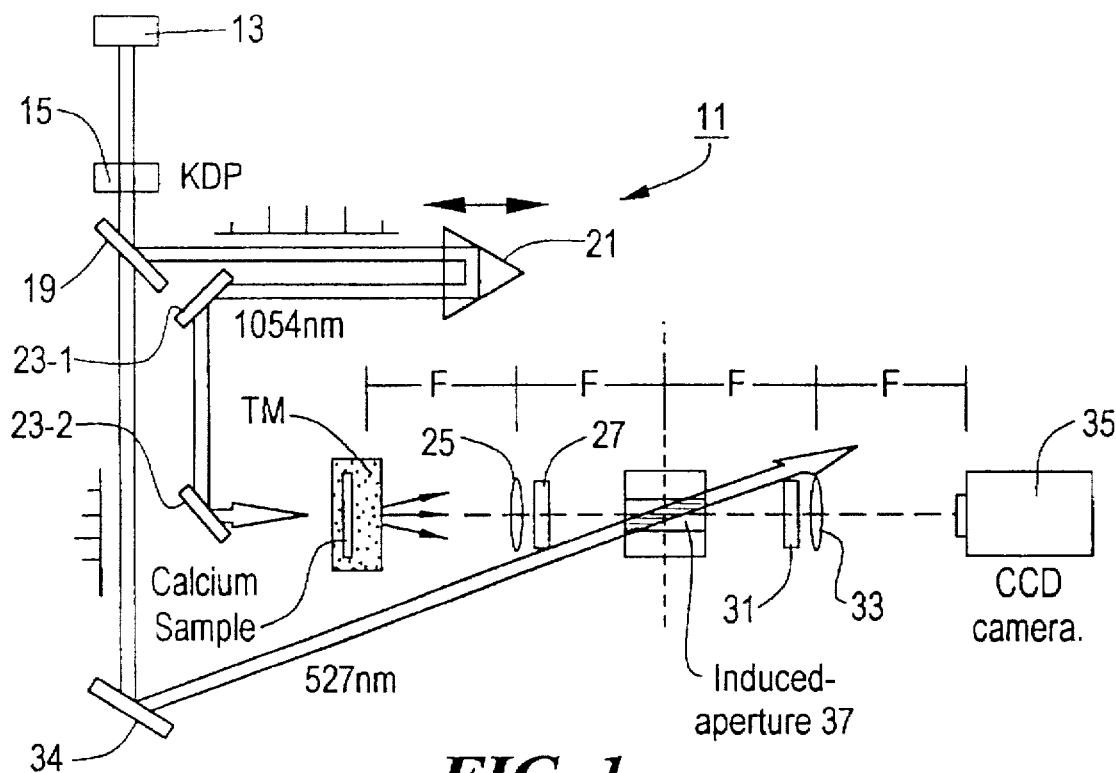
FIG. 1 is a schematic view of one embodiment of an optical imaging system constructed for performing the method of the present invention.

Referring now to FIG. 1, there is shown a schematic view of an experimental system that may be used, in accordance with the teachings of the present invention, to optically image a turbid medium, such as a breast tissue, containing one or more calcifications, the system being represented generally by reference numeral 11.

System 11 comprises a mode-locked laser 13 for emitting a series of laser pulses. The laser pulses have a peak power of $5 \times 10^8$ W, a duration time of 8 ps and a wavelength of 1054 nm. The pulse energy is ~8 mJ. The beam of 1054 nm pulses is sent through a KDP crystal 15 to produce the second harmonic at 527 nm. A dichroic beam-splitter 19 reflects the 1054 nm beam component and transmits the 527 nm beam component. The 1054 nm component is transmitted through a delay unit 21, reflected off a pair of mirrors 23-1 and 23-2 and used to illuminate a turbid medium TM containing one or more calcifications.

Figure 2:
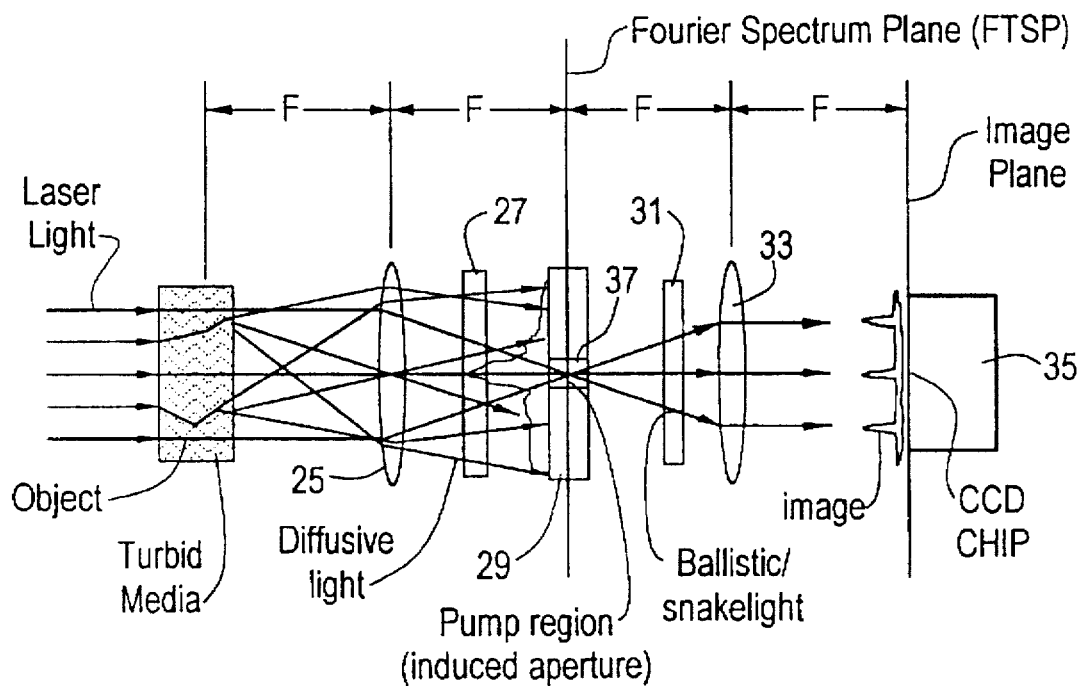
FIG. 2 is an enlarged schematic view of a portion of the system of FIG. 1.
Figures 3A, 3B:
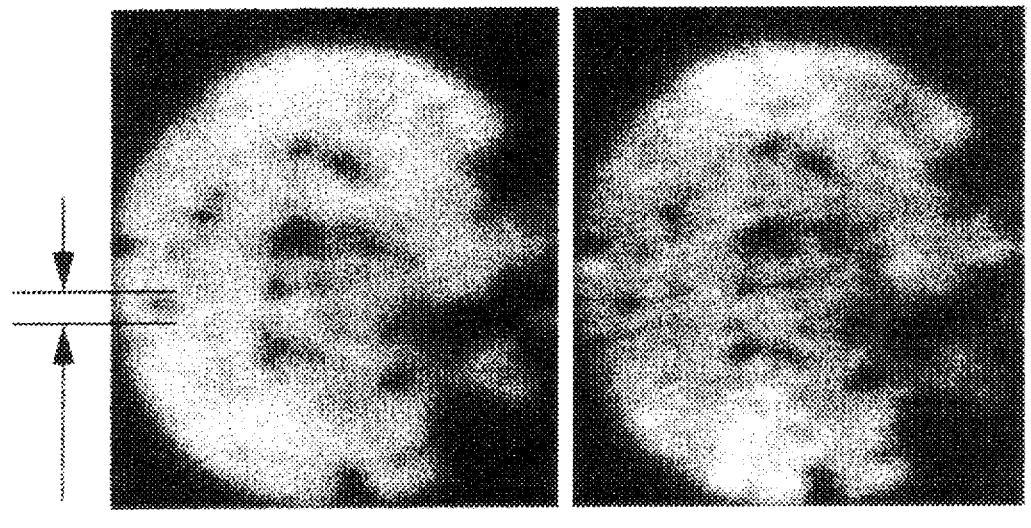
FIGS. 3(a) through 3(d) are images obtained using the system of FIG. 1 for samples of (a) clear water containing calcium pills, (b) 2% diluted Intralipid stock solution containing calcium pills, (c) clear water containing calcium carbonate particles, and (d) 2% diluted Intralipid stock solution containing calcium carbonate particles, respectively, each sample being contained within a 5-cm thick cell, the samples being probed by a 1054-nm, 8-ps probe pulse with 0-ps gate delay, the Kerr gate being opened by a 527-nm gating pulse.
Figures 3C, 3D:
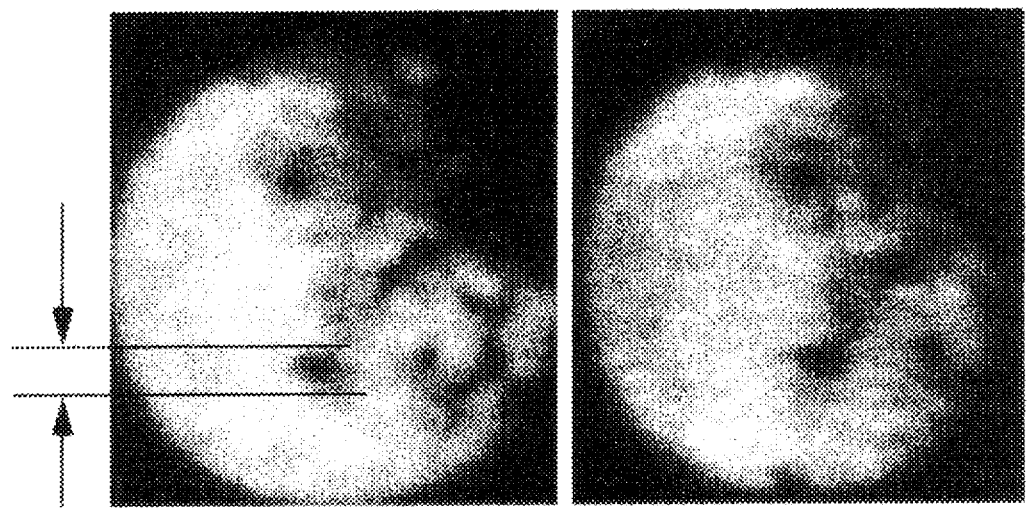

System 11 also includes a 4F imaging system (see also FIG. 2) for imaging the light emergent from the opposite side of the turbid medium TM. The 4F imaging system comprises a focusing lens 25 positioned at 1F, a Kerr gate comprising a polarizer 27, a Kerr cell 29 positioned at 2F and an analyzer 31, an imaging lens 33 positioned at 3F and a CCD camera 35 positioned at 4F. The typical transmission efficiency of the Kerr gate is about 5%. CCD camera 35 is coupled to a monitor or other display (not shown) for use in displaying the image of light detected by CCD camera 35. A time-gated image intensifier (not shown) coupled to a CCD camera can also be used to measure 2D images at various time slices to obtain images of calcification regions, and tumors of the breast.

The 527 nm beam component, which is reflected off a mirror 34 and arrives at Kerr cell 29 synchronously with the arrival of the ballistic and snake-like components of the emergent light from the turbid medium TM, is used to pump only that portion of Kerr cell 29 located at the 2F focal point.

In this manner, an induced aperture is effectively created in the Kerr cell 29, which temporally and spatially gates the light emergent from the turbid medium TM.

Referring now to FIGS. 3(a) through 3(d), there are shown various images obtained using the system of FIG. 1 of samples of (a) clear water containing calcium particles derived from calcium pills, (b) 2% diluted Intralipid stock solution containing calcium particles derived from calcium pills, (c) clear water containing calcium carbonate particles, and (d) 2% diluted Intralipid stock solution containing calcium carbonate particles, respectively, each sample being contained within a 5-cm thick cell, the calcium particles ranging in size from about 0.1 to 0.5 mm. (The transport mean free path of 2% diluted Intralipid solution is about 2 mm at 530 nm and is similar to that for human breast tissues.) The dark shadow regions in the figures represent the calcium particles. The light shadow regions were caused by glue which was used to fix calcium particles on a transparent glass slide.

The CCD camera used to detect the images was a cooled CCD camera system with 16 bit resolution controlled by a Mac IIci from Photometrics Inc. The minimum detectability of the time gated signal level was about 3 counts per pixel above the dark current level. This allowed about $10^-$ attenuation of the incident 1054 nm laser beam intensity through the Intralipid solution. Due to light scattering, the measured transport mean free path of 2% Intralipid solution at 1054 nm was about 4.5 mm which is approximately twice longer than that from the 527 nm. The use of infrared illumination can penetrate more than twice the thickness of the turbid media than the use of visible light source.

As can be seen, there are several important aspects, observations, applications, advantages and/or comments relating to the present invention, the following being illustrative thereof:

(a) To use optical techniques to find regions and image calcification regions of size about 0.03 to 5 mm in breasts.

(b) To use optical techniques to find regions and image calcification regions of size about 0.03 to 5 mm in breasts using wavelengths from about 700 to 1350 nm.

(c) To use optical techniques to measure sizes of spatial distributions and patterns of calcifications in breast in order to determine if the region is cancerous or not.

(d) To use optical techniques to measure sizes of spatial distributions and patterns of calcifications in breast in order to determine if the region is cancerous or not using wavelength between about 700 to 1350 nm.

(e) The shape of calcification regions imaged by optical techniques in breasts can be used to diagnose tumors as being cancerous or benign.

(f) The calcification regions appear as shadows with size of about 0.03 to 5 mm using optical techniques.

(g) Use CCD camera with time-gated image intensifier on 80 ps to 10 ns time scale.

(h) Use ultrafast time and the space gates from optical and electronic means in the time domain of about $10^{-10}$ to $10^{-14}$ seconds to image calcification regions in breasts.

(i) Use space gate to image calcification regions in breasts at wavelengths from about 700 to 1350 nm.

(j) Add column on time-gated image intensifier with CCD camera computer system to image. Ultrafast optical gates including optical Kerr gate, upper-conversion gate, electron gate include the time-gated image intensifier with CCD camera (80 ps to 10 ns) or streak camera, phase-conjugation gate, and other nonlinear optical gates. Electronic gates include image intensifier with $\geq$80-ps and streak camera to image calcifications in breasts.

(k) Use optical Fourier transformation and spatial aperture to modify spatial frequency at the Fourier plane of the time-gate to further filter late diffusive noise of signal from breast to identify calcification regions in breasts.

(l) Place time-gate at the Fourier plane to select and modify image spatial frequencies of the early ballistic/snake light.

(m) Use laser field induced optical apertures for a means of the spatial aperture made out of a small hole from a metal plate.

(n) Use continuous wave (CW) or pulsed laser light with wavelength in the region between about 700 to 1350 nm.

(o) Use two cascaded stage Kerr gates to couple with two Fourier spatial filters to image early ballistic/snake signals and remove later diffusive light of calcification regions in breast.

(p) Use multiple (2 or more) time gates in sequences in conjunction with spatial filters to remove late diffusive noise. Each time gate is placed at the 2F Fourier places for time-space gating of ballistic/snake light of calcification in breasts.

(q) Use 4F Fourier spatial filtering to improve the image quality. Use zoom-lenses in the 4F Fourier imaging system to compensate the thickness variation of the sample.

(r) The 2D patterns of images of the calcification regions in breasts can be used to determine whether a shadow region is a cancerous region.

(s) Use cooled 2D video detectors to image ballistic/snake signals or diffusive light in the region between about 700-nm to 1350-nm of calcification regions in breast to diagnose cancer regions.

(t) Use single ray scanning method to reconstruct the 3-D image from ballistic/snake signals of calcification regions in breasts.

(u) Use wavelength coding and time sequence coding to the single ray scanning 3D imaging to improve the accuracy.

(v) Use imaging disparity through angular displacement from two 2D ballistic/snake images to reconstruct 3D stereographic image of calcification regions in breasts.

(w) Use angular coding in sequence or in parallel to introduce image disparity for the 2D ballistic/snake images of calcification regions in breasts.

(x) Use either sequential or parallel polarization coding to display ballistic/snake 3D stereoscopic images of calcification in breasts.

(y) Use a fast processing/display (<0.05 seconds) and a slow processing/display (>0.1 seconds) video systems to image the ballistic/snake images of calcification in breast. The fast display video system will provide a fast and rough image for the alignment and safety monitoring. The slow display video system will provide a long signal average for better sensitivity and accuracy. These two (slow and fast) imaging systems will obtain the transmitted ballistic/snake signals using optical beam splitter, mechanical mirror in and out, or electronic spitting from a video camera system.

(z) Use high repetition rate and high scanning rate to reduce the photon fluence for safety radiation and to increase the signal averaging of calcification regions in breasts.

(aa) Use single coherent fiber bundle for single beam non-scanning illumination to acquire ballistic/snake images of calcification in breasts.

(bb) Use single beam and opt-mechanical scanning method for 2-D mapped illumination to acquire ballistic/snake images of calcification in breasts.

(cc) Use multiple beam for 2D non-scanning illumination of calcification regions in breasts.

(dd) Use lasers spectra region between about 700 to 1350 nm to image calcification regions in breasts such as Ti:sapphire, $Cr^{4+}$:Forsterite, $Cr^{4+}$:YAG, $Cr^{4+}$:$CaCeO_3$, or semiconductor lasers.

(ee) Use grid filtering to collect time-gated signals of calcification regions in breasts.

(ff) Use collimator to collect time-gated signals of calcification regions in breasts.

(gg) Use video cassette recorder for massive analog 2D ballistic/snake image recording and storage of calcification regions in breasts.

(hh) Use 2D coherent-fiber-CCD assembly for direct 2D and 3D time-gated ballistic imaging of calcification regions in breasts.

(ii) Use color-filtered time-gated signals for computer aided medical analysis of calcification regions in breasts.

(jj) Identify malignant and benign tissues from calcifications and normal regions by examining size and structures of calcifications using shadowgram taken with the time-spatial gate imaging system.

(kk) Identify malignant and benign tissues from calcifications and normal regions by examining number of calcifications using shadowgrams taken with the time-spatial gate imaging system.

(ll) Identify malignant and benign tissues from calcifications and normal regions by examining 2D shape differences of calcifications using time-spatial gate imaging system.

(mm) The shape of calcification patterns on image is in the form of shadow tree whether the tumor is malignant in breasts removed with optical gate.

(nn) Identify malignant and benign breast tissues from shape, size, and structures of calcifications and normal regions by examining attenuation caused by calcification density using time-spatial gate imaging system.

(oo) Identify malignant and benign breast tissues from calcifications and normal regions by examining 2D shadowgram pattern differences of calcifications using time-spatial gate imaging system.

(pp) Identify malignant and benign breast tissues from calcifications and normal regions by examining 2D shadowgram spatial distribution differences of calcifications using time-spatial gate imaging system.

(qq) Identify malignant and benign breast tissues from calcifications by examining Fourier spatial spectrum differences caused by the differences of size, shape, distribution, pattern, and density of calcifications using time-spatial gate imaging system.

(rr) Identify malignant and benign breast tissues from calcifications and normal regions by using different spatial filter, aperture, and masks in Fourier spectrum plane for different types of calcifications using time-spatial gate imaging system.

(ss) A time-gate image intensifier (of 80 ps to 5 nsec) coupled to CCD camera can be used to obtain an image shadowgram to see calcification and breast tissue.

(tt) Spectral images at two or more wavelengths to get difference images of calcification region and tumor for better breast screening. Wavelengths are selected at water, lipids, calcification absorption in 700 to 1350 nm region (see F. Marks article for lipids and water).

(uu) The regions of calcification are measured to determine whether growth should be biopsied or removed.

(vv) Optical transillumination shadowgram for calcification region in breasts is used as a diagnostic approach to diagnose breast cancer.

(ww) Optical imaging breast for calcification regions is used as a way for diagnosis or breast screening.

The embodiments of the present invention recited herein are intended to be merely exemplary and those skilled in the art will be able to make numerous variations and modifications to it without departing from the spirit of the present invention. All such variations and modifications are intended to be within the scope of the present invention as defined by the claims appended hereto.

What is claimed is:

1. A method for imaging a turbid medium containing one or more calcifications, said method comprising the steps of:

(a) illuminating at least a portion of the turbid medium containing at least one calcification with light, whereby light emerges from the turbid medium consisting of a ballistic component, a snake-like component and a diffuse component;

(b) gating the emergent light to preferentially pass the ballistic and/or snake-like components; and (c) using the gated light to form an image of the at least one calcification within the illuminated portion of the turbid medium.

2. The method as claimed in claim 1 wherein the illuminating light is a pulse of light.

3. The method as claimed in claim 1 wherein the illuminating light is laser light.

4. The method as claimed in claim 3 wherein the illuminating light is emitted from a laser selected from the group consisting of Ti:sapphire, $Cr^{4+}$:Forsterite, $Cr^{4+}$:YAG, $Cr^{4+}$:$CaCeO_3$ and semiconductor lasers.

5. The method as claimed in claim 1 wherein the illuminating light is a pulse of laser light.

6. The method as claimed in claim 5 wherein the illuminating light is a pulse of laser light having a wavelength in the range of about 700 nm to about 1350 nm.

7. The method as claimed in claim 1 wherein the illuminating light has a wavelength in the range of about 700 nm to about 1350 nm.

8. The method as claimed in claim 1 wherein said illuminating step comprises illuminating at a first wavelength in the range of about 700 nm to about 1350 nm and then illuminating at a second wavelength different from said first wavelength and in the range of about 700 nm to about 1350 nm, wherein said gating step comprises gating the emergent light of said first wavelength and then gating the emergent light of said second wavelength and wherein said using step comprises using a difference of the images formed with the gated light of said first and second wavelengths to form a spectral difference image.

9. The method as claimed in claim 1 wherein the turbid medium is a tissue sample.

10. The method as claimed in claim 9 wherein the tissue sample is a human breast tissue sample and wherein said one or more calcifications range in size from about 0.03 to about 5 mm.

11. The method as claimed in claim 1 wherein said gating step comprises temporally gating the emergent light to preferentially pass the ballistic and snake-like components.

12. The method as claimed in claim 1 wherein said gating step comprises spatially gating the emergent light to preferentially pass the ballistic and snake-like components.

13. The method as claimed in claim 1 wherein said gating step comprises temporally and spatially gating the emergent light to preferentially pass the ballistic and snake-like components.

14. The method as claimed in claim 13 wherein said gating step comprises passing the emergent light through a Kerr gate, the Kerr gate including a Kerr cell positioned at the 2F spectral plane of a 4F Fourier imaging system, and pumping, for an appropriate period of time, only that portion of the Kerr cell situated at the focal point of the 4F Fourier imaging system.

15. The method as claimed in claim 1 wherein said image is a shadowgram.

16. The method as claimed in claim 1 wherein said image is a 3D stereoscopic image.

17. A method for detecting the presence of one or more calcifications within a portion of a turbid medium, said method comprising the steps of:
   (a) illuminating at least said portion of the turbid medium with light, whereby light emerges from the turbid medium consisting of a ballistic component, a snake-like component and a diffuse component;
   (b) gating the emergent light to preferentially pass the ballistic and/or snake-like components;
   (c) using the gated light to form an image of the illuminated portion of the turbid medium; and
   (d) examining the image for the presence of one or more calcifications.

18. The method as claimed in claim 17, wherein the illuminating light is a pulse of light.

19. The method as claimed in claim 18 wherein said gating step comprises temporally gating the emergent light to preferentially pass the ballistic and snake-like components.

20. The method as claimed in claim 18 wherein said gating step comprises spatially gating the emergent light to preferentially pass the ballistic and snake-like components.

21. The method as claimed in claim 18 wherein said gating step comprises temporally and spatially gating the emergent light to preferentially pass the ballistic and snake-like components.

22. The method as claimed in claim 21 wherein said gating step comprises passing the emergent light through a Kerr gate, the Kerr gate including a Kerr cell positioned at the 2F spectral plane of a 4F Fourier imaging system, and pumping, for an appropriate period of time, only that portion of the Kerr cell situated at the focal point of the 4F Fourier imaging system.

23. The method as claimed in claim 18 wherein said image is a shadowgram.

24. The method as claimed in claim 18 wherein said image is a 3D stereoscopic image.

25. The method as claimed in claim 17 wherein the illuminating light is laser light.

26. The method as claimed in claim 25 wherein the illuminating light is emitted from a laser selected from the group consisting of Ti:sapphire, $Cr^{4+}$:Forsterite, $Cr^{4+}$:YAG, $Cr^{4+}$:$CaCeO_3$ and semiconductor lasers.

27. The method as claimed in claim 17 wherein the illuminating light is a pulse of laser light.

28. The method as claimed in claim 17 wherein the illuminating light is a pulse of laser light having a wavelength in the range of about 700 nm to about 1350 nm.

29. The method as claimed in claim 17 wherein the illuminating light has a wavelength in the range of about 700 nm to about 1350 nm.

30. The method as claimed in claim 17 wherein the turbid medium is a tissue sample.

31. The method as claimed in claim 30 wherein the tissue sample is a human breast tissue sample and wherein said one or more calcifications range in size from about 0.03 to about 5 mm.

32. The method as claimed in claim 30 wherein the turbid medium is a tissue sample selected from the group consisting of breast tissue, brain tissue and prostate tissue.

33. A method for cancer-screening a tissue, said method comprising the steps of:
   (a) illuminating at least a portion of a tissue with light, whereby light emerges therefrom consisting of a ballistic component, a snake-like component and a diffuse component;
   (b) gating the emergent light to preferentially pass the ballistic and/or snake-like components;
   (c) using the gated light to form an image of the illuminated portion of the tissue; and
   (d) examining the image for the presence of calcifications suggestive of cancer.

34. The method as claimed in claim 33 wherein the tissue is selected from the group consisting of breast tissue, brain tissue and prostate tissue.

35. The method as claimed in claim 33 wherein the tissue is breast tissue.

36. The method as claimed in claim 35 wherein the illuminating light is a pulse of light.

37. The method as claimed in claim 35 wherein the illuminating light is laser light.

38. The method as claimed in claim 35 wherein the illuminating light is emitted from a laser selected from the group consisting of Ti:sapphire, $Cr^{4+}$:Forsterite, $Cr^{4+}$:YAG, $Cr^{4+}$:$CaCeO_3$ and semiconductor lasers.

39. The method as claimed in claim 35 wherein the illuminating light is a pulse of laser light.

40. The method as claimed in claim 35 wherein the illuminating light is a pulse of laser light having a wavelength in the range of about 700 nm to about 1350 nm.

41. The method as claimed in claim 35 wherein the illuminating light has a wavelength in the range of about 700 nm to about 1350 nm.

42. The method as claimed in claim 35 wherein said gating step comprises temporally gating the emergent light to preferentially pass the ballistic and/or snake-like components.

43. The method as claimed in claim 35 wherein said gating step comprises spatially gating the emergent light to preferentially pass the ballistic and/or snake-like components.

44. The method as claimed in claim 35 wherein said gating step comprises temporally and spatially gating the emergent light to preferentially pass the ballistic and/or snake-like components.

45. The method as claimed in claim 44 wherein said gating step comprises passing the emergent light through a Kerr gate, the Kerr gate including a Kerr cell positioned at the 2F spectral plane of a 4F Fourier imaging system, and pumping, for an appropriate period of time, only that portion of the Kerr cell situated at the focal point of the 4F Fourier imaging system.

46. The method as claimed in claim 35 wherein said image is a shadowgram.

47. The method as claimed in claim 35 wherein said image is a 3D stereoscopic image.

48. The method as claimed in claim 35 wherein said illuminating step comprises illuminating a first side of the breast tissue and wherein said image is formed using light emergent from a second side of the breast tissue, said second side of the breast tissue being opposite to the first side thereof.

49. A method for imaging a turbid medium containing one or more calcifications, said method comprising the steps of:
(a) illuminating at least a portion of the turbid medium containing at least one calcification with light, whereby light consisting of a ballistic component, a snake component and a diffuse component emerges from the turbid medium; and
(b) forming an image of the at least one calcification within the illuminated portion of the turbid medium with the emergent light.

50. The method as claimed in claim 49 wherein said turbid medium is a tissue.

51. The method as claimed in claim 50 wherein said tissue is selected from the group consisting of breast tissue, brain tissue and prostate tissue.

52. The method as claimed in claim 51 wherein said tissue is breast tissue.

53. The method as claimed in claim 49 wherein said illuminating light is a pulse of laser light having a wavelength in the range of about 700 nm to about 1350 nm.

54. A method for detecting the presence of one or more calcifications within a portion of a turbid medium, said method comprising the steps of:
(a) illuminating at least said portion of the turbid medium with light, whereby light emerges from the turbid medium consisting of a ballistic component, a snake-like component and a diffuse component;
(b) forming an image of the illuminated portion of the turbid medium with the emergent light; and
(c) examining the image for the presence of one or more calcifications.

55. The method as claimed in claim 54 wherein said turbid medium is a tissue.

56. The method as claimed in claim 55 wherein said tissue is selected from the group consisting of breast tissue, brain tissue and prostate tissue.

57. The method as claimed in claim 56 wherein said tissue is breast tissue.

58. The method as claimed in claim 54 wherein said illuminating light is a pulse of laser light having a wavelength in the range of about 700 nm to about 1350 nm.

59. A method for cancer-screening a breast tissue, said method comprising the steps of:
(a) illuminating at least a portion of a breast tissue with light, whereby light emerges therefrom consisting of a ballistic component, a snake-like component and a diffuse component;
(b) forming an image of the illuminated portion of the breast tissue with the emergent light; and
(c) examining the image for the presence of calcifications suggestive of cancer.

60. A method for imaging a turbid medium containing one or more calcifications, said method comprising the steps of:
(a) illuminating at least a portion of the turbid medium containing at least one calcification with light, whereby light consisting of a ballistic component, a snake component and a diffuse component emerges from the turbid medium; and
(b) forming an image of the at least one calcification within the illuminated portion of the turbid medium using the diffusive component of the emergent light or a portion of the diffusive component of the emergent light, but not the ballistic or snake components.

61. The method as claimed in claim 60 wherein said turbid medium is a tissue.

62. The method as claimed in claim 61 wherein said tissue is selected from the group consisting of breast tissue, brain tissue and prostate tissue.

63. The method as claimed in claim 62 wherein said tissue is breast tissue.

64. The method as claimed in claim 60 wherein said illuminating light is a pulse of laser light having a wavelength in the range of about 700 nm to about 1350 nm.

65. A method for detecting the presence of one or more calcifications within a portion of a turbid medium, said method comprising the steps of:
(a) illuminating at least said portion of the turbid medium with light, whereby light emerges from the turbid medium consisting of a ballistic component, a snake-like component and a diffuse component;
(b) forming an image of the illuminated portion of the turbid medium using the diffusive component of the emergent light or a portion of the diffusive component of the emergent light, but not the ballistic or snake components; and
(c) examining the image for the presence of one or more calcifications.

66. The method as claimed in claim 65 wherein said turbid medium is a tissue.

67. The method as claimed in claim 66 wherein said tissue is selected from the group consisting of breast tissue, brain tissue and prostate tissue.

68. The method as claimed in claim 67 wherein said tissue is breast tissue.

69. The method as claimed in claim 65 wherein said illuminating light is a pulse of laser light having a wavelength in the range of about 700 nm to about 1350 nm.

70. A method for cancer-screening a breast tissue, said method comprising the steps of:
(a) illuminating at least a portion of a breast tissue with light, whereby light emerges therefrom consisting of a ballistic component, a snake-like component and a diffuse component;
(b) forming an image of the illuminated portion of the breast tissue using the diffusive component of the emergent light or a portion of the diffusive component of the emergent light, but not the ballistic or snake-like components; and
(c) examining the image for the presence of calcifications suggestive of cancer.

71. The method as claimed in claim 70 wherein said forming step comprises detecting cw, time-sliced diffusive component.

72. The method as claimed in claim 70 wherein said forming step comprises temporally and/or spatially gating the emergent light to preferentially pass portions of diffusive light.

73. The method as claimed in claim 72 wherein said gating step comprises passing the emergent light through a time-gated image intensifier CCD camera to display an image.

74. The method as claimed in claim 70 wherein said image is a 3D stereoscopic image from multiple views.

* * * * *